(12) United States Patent
Mullejans et al.

(10) Patent No.: US 7,819,850 B2
(45) Date of Patent: Oct. 26, 2010

(54) OSTOMY APPLIANCE AND A COMPACTED BAG

(75) Inventors: Peter Mullejans, Aalsgaarde (DK); Michael Hansen, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 750 days.

(21) Appl. No.: 10/591,737

(22) PCT Filed: Mar. 1, 2005

(86) PCT No.: PCT/DK2005/000144

§ 371 (c)(1), (2), (4) Date: Aug. 6, 2007

(87) PCT Pub. No.: WO2005/082272

PCT Pub. Date: Sep. 9, 2005

(65) Prior Publication Data

US 2008/0004580 A1    Jan. 3, 2008

(30) Foreign Application Priority Data

Mar. 1, 2004 (DK) ................. 2004 00344
May 28, 2004 (DK) ................. 2004 00849

(51) Int. Cl.
*A61F 5/44* (2006.01)

(52) U.S. Cl. ..................................... 604/344

(58) Field of Classification Search ............... 604/317, 604/327, 332, 338–344; 264/454
See application file for complete search history.

(56) References Cited

U.S. PATENT DOCUMENTS

| | | | |
|---|---|---|---|
| 4,367,732 A | 1/1983 | Poulsen et al. | |
| 4,449,970 A | 5/1984 | Bevan et al. | |
| 4,710,183 A | 12/1987 | Steer | |
| 4,714,465 A | 12/1987 | Steer | |
| 4,816,027 A | 3/1989 | Gilchrist et al. | |
| 5,051,259 A | 9/1991 | Olsen et al. | |
| 5,209,744 A | 5/1993 | Abe et al. | |
| 5,306,264 A | 4/1994 | Ferguson et al. | |
| 5,423,782 A * | 6/1995 | Wolrich ................. | 604/339 |
| 5,426,782 A | 6/1995 | Shiga | |
| 5,496,297 A | 3/1996 | Olsen | |
| 5,591,144 A * | 1/1997 | Smith et al. ............. | 604/327 |
| 5,690,622 A | 11/1997 | Smith et al. | |
| 5,690,623 A | 11/1997 | Lenz et al. | |
| 5,714,225 A | 2/1998 | Hansen et al. | |
| 5,785,695 A | 7/1998 | Sato et al. | |
| 5,800,415 A | 9/1998 | Olsen | |
| 5,865,819 A * | 2/1999 | Cisko et al. ............. | 604/339 |
| 5,938,647 A | 8/1999 | Smith | |

(Continued)

FOREIGN PATENT DOCUMENTS

CA    1 108 958    9/1981

(Continued)

*Primary Examiner*—Tatyana Zalukaeva
*Assistant Examiner*—Benedict L Hanrahan
(74) *Attorney, Agent, or Firm*—Jacobson Holman PLLC

(57) ABSTRACT

An ostomy appliance is provided having a receiving member and a disposable bag liner, as well as a method for producing a compacted inner bag liner, and a method for applying such an ostomy appliance. The inner bag is compacted lengthwise while twisting a bottom part in relation to a rim, with the method including the manner of compacting the same.

25 Claims, 12 Drawing Sheets

U.S. PATENT DOCUMENTS

| | | |
|---|---|---|
| 6,171,594 B1 | 1/2001 | Nielsen |
| 6,303,700 B1 | 10/2001 | Chen |
| 6,312,415 B1 | 11/2001 | Nielsen et al. |
| 6,437,038 B1 | 8/2002 | Chen |
| 6,451,883 B1 | 9/2002 | Chen et al. |
| 6,685,683 B1 | 2/2004 | Clok et al. |
| 2004/0064132 A1* | 4/2004 | Boehringer et al. .......... 604/543 |
| 2006/0200101 A1* | 9/2006 | Mullejans et al. ........... 604/339 |

FOREIGN PATENT DOCUMENTS

| | | |
|---|---|---|
| DE | 1 947 368 | 4/1971 |
| DE | 195 19 069 A1 | 11/1996 |
| DE | 199 21 555 A1 | 2/2000 |
| DE | 203 08 266 U1 | 8/2003 |
| DE | 20 2004 000 323 U1 | 5/2004 |
| DK | 2003 00409 | 9/2004 |
| EP | 0 259 184 B1 | 3/1988 |
| EP | 0 320 895 A1 | 6/1989 |
| EP | 0 703 762 B1 | 4/1996 |
| EP | 0 747 026 B1 | 12/1996 |
| EP | 0 768 848 B1 | 4/1997 |
| EP | 0 768 849 B1 | 4/1997 |
| EP | 0 821 925 B1 | 2/1998 |
| EP | 1 290 994 A2 | 3/2003 |
| FR | 2 476 481 A1 | 8/1981 |
| GB | 2 265 832 A | 10/1993 |
| GB | 2 306 889 A | 5/1997 |
| HU | 190 848 | 11/1986 |
| WO | WO 91/01118 | 2/1991 |
| WO | WO 91/01119 | 2/1991 |
| WO | WO 93/18725 | 9/1993 |
| WO | WO 94/12128 | 6/1994 |
| WO | WO 94/18919 | 9/1994 |
| WO | WO 96/01090 | 1/1996 |
| WO | WO 99/30652 | 6/1999 |
| WO | WO 00/30576 | 6/2000 |
| WO | WO 00/54820 | 9/2000 |
| WO | WO 00/67683 | 11/2000 |
| WO | WO 01/05340 A2 | 1/2001 |
| WO | WO 01/10363 A1 | 2/2001 |
| WO | WO 01/21115 A1 | 3/2001 |
| WO | WO 01/54632 A1 | 8/2001 |
| WO | WO 01/82846 A1 | 11/2001 |
| WO | WO 02/058603 A1 | 8/2002 |
| WO | WO 2004/082452 A2 | 9/2004 |

* cited by examiner

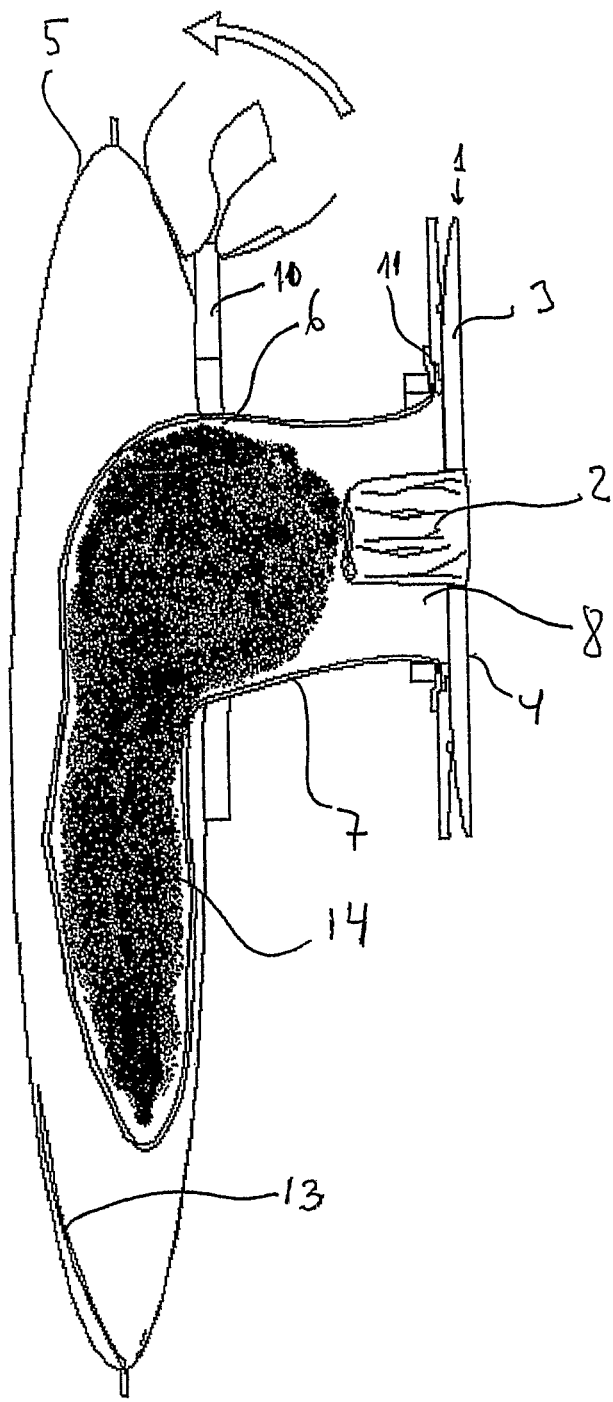
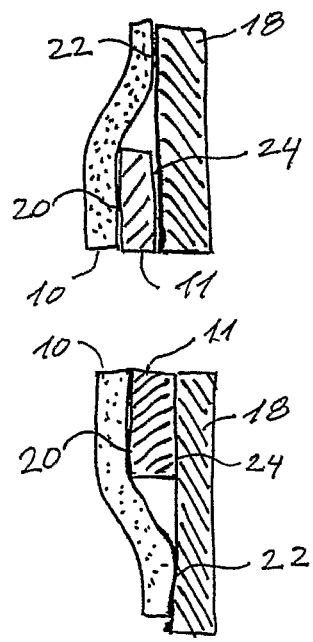
Fig. 3a
Fig. 3b

OSTOMY APPLIANCE AND A COMPACTED BAG

This is a nationalization of PCT/DK2005/000144 filed 1 Mar. 2005 and published in English.

FIELD OF THE INVENTION

The present invention relates to an ostomy appliance comprising a receiving member and a disposable bag liner, a method for producing a compacted inner bag liner, and a method for applying such an ostomy appliance. Furthermore, the present invention relates to a bag being compacted lengthwise while twisting a bottom part in relation to a rim and a method of compacting the same.

BACKGROUND OF THE INVENTION

It is known in the art to provide ostomy appliances having an outer bag and a flushable inner bag. Such an appliance is known from the applicant's own publication WO 01/82846.

Other ostomy appliances may be seen in EP 0 768 848, EP 0 703 762, EP 0 768 848, GB 2 306 889, EP 0 821 925 and U.S. Pat. No. 5,423,782.

It may be seen as an object of the present invention to provide an inner bag liner which is folded in a way that minimises the risk of "pancaking" and blocking of the bag when the inner bag liner is automatically gradually unfolded or stretched by the waste material first contacting the bottom of the inner bag liner and pressing the same down into the receiving bag.

It may also be seen as an object of the present invention to provide a collecting bag that is flushable. Furthermore, it may be seen as an object of the present invention to provide an inner bag liner which is compacted without being pulled over a surface (which is also present in the use situation) and thus no friction between the surface and the inner bag liner may limit the unfolding of the bag in the use situation.

Furthermore, it may also be seen as an object of the present invention to provide a bag compacted such that it may unfold without pancaking and a method for compacting a bag.

DESCRIPTION OF THE INVENTION

In a FIRST ASPECT the present invention relates to an ostomy appliance comprising a base plate, said base plate having a first hole for receiving a stoma, ureter, or catheter and an adhesive wafer having a first surface to be attached to the wearer's abdomen, back, or chest; a receiving member releasably attached to the base plate, said member having a second hole for receiving wastes exiting the stoma, ureter or catheter; and a disposable inner bag liner forming a second bag inside the receiving member and being releasably attachable to the base plate in a first coupling area by first coupling means, said disposable inner bag liner having a third hole for receiving wastes exiting the stoma, ureter or catheter and the receiving member being releasably attachable to the base plate in a second coupling area by second coupling means, the first coupling means being in the form of an adhesive flange projecting from a rim of the third hole and having a surface for releasable sealing against a second surface of the base plate facing away from the user, wherein the inner bag liner is provided with folding lines for compacting the bag lengthwise, and wherein said folding lines form spiral lines when the bag is compacted in a lengthwise rotational movement.

The receiving member may be a bag allowing the disposable inner bag liner to form a second bag inside the receiving member.

In one embodiment of the invention the second coupling means is in the form of an adhesive flange projecting from the rim of the second hole of the receiving member and having a surface for adhesive sealing against the second surface of the base plate. In the latter embodiment the flange of the receiving member has a skin facing surface and an opposite outer surface. The skin facing surface may be adapted to adhere to the base plate or a flange of the same. Furthermore, the skin facing surface may be adapted to adhere to the flange of the inner bag liner.

The outer diameter of the first coupling means may be greater than the inner diameter of the second coupling means which allows the use together with coupling means in the form of matching adhesive flanges and also in the form of matching coupling rings. The outer diameter of the flange of the inner bag liner may be larger than the inner diameter of the receiving member and thus an over-lap is possible. Furthermore, it makes it possible to apply a new inner bag liner to the receiving member prior to attachment of said receiving member to the base plate or a surface thereof.

The peel strength of the adhesive sealing of the first coupling means could be greater than the peel strength of the second couplings means. This renders it easy selectively to detach the receiving member leaving the inner bag liner attached to a base plate. This may be effected by providing the flange with release properties on the surface facing the receiving member.

In one embodiment the second coupling means of the receiving member in a third coupling area is releasable attachable to the flange of the disposable inner bag liner, and the peel strength of the adhesive sealing in the first coupling area is greater than the peel strength in the third coupling area. As the adhesive forces between the flange of the inner bag liner and the flange of the base plate (i.e. in the first coupling area) are stronger than the adhesive forces between the flange of the receiving member and the flange of the inner bag liner (i.e. in the third coupling area) it is possible to remove the receiving member without also removing the inner bag liner.

In one embodiment the flange of the inner bag liner is provided with a siliconized surface on the side facing the flange of the receiving member in the third coupling area so as to provide smaller adhesive forces between the flange of the receiving member and the flange of the inner bag liner than between the flange of the inner bag liner and the flange of the base plate.

In another embodiment of the invention, the second coupling means is in the form of one or more coupling rings, and the outer diameter of the first coupling means is smaller than the inner diameter of the second coupling means.

When the inner bag liner stays attached to the base plate, it acts as a drip-catcher and while the user attaches a fresh inner bag liner to the receiving member which may be reused several times. The inner bag liner will thus reduce the risk of escaping odour or soiling of the clothing by dripping output from the stoma.

Thus, the user may easily flush the contents of the receiving member in the WC and is not left with a soiled receiving member but rather with a receiving member, which may be used again or be disposed in a waste bin without obnoxious smells.

This is especially advantageous for people living in flats and people bothered by leaving used ostomy bags giving rise to obnoxious smells in public toilets or at work or who might empty a used bag before disposing the same in the waste bin.

It is advantageous to provide the inner bag liner with a membrane allowing intestinal gas to escape from the inner bag but being impermeable to liquids in order to avoid ballooning. The use of an inner bag liner will in itself prolong the active service time of a filter of a receiving member as the contents of the receiving member is separated physically from the filter reducing the risk of blocking.

The inner bag liner may be used with all types of stomas but the advantages are most pronounced in connection with colostomies and in particular ileo-ostomies where the users typically exchange receiving members two to three times a day.

In a SECOND ASPECT the invention relates to an ostomy appliance comprising an adhesive wafer, said adhesive wafer having a first hole for receiving a stoma, ureter, or catheter, said adhesive wafer having a first surface to be attached to the wearer's abdomen, back, or chest and a receiving member attached to the adhesive wafer, said member having a second hole for receiving wastes exiting the stoma, ureter or catheter; and a disposable inner bag liner forming a second bag inside the receiving member and being releasably attachable to the adhesive wafer by first coupling means, said disposable inner bag liner having a third hole for receiving wastes exiting the stoma, ureter or catheter, the first coupling means being in the form of an adhesive flange projecting from a rim of the third hole and having a surface for releasable sealing against a first surface of the adhesive wafer, wherein the inner bag liner is provided with folding lines for compacting the bag lengthwise, and wherein said folding lines form spiral lines when the bag is compacted in a lengthwise rotational movement.

In the following further features and elements of the first and second aspect are described in further detail.

In one embodiment of the invention the inner bag liner is compacted lengthwise to form a disc-like structure having an outer diameter less than the inner diameter of the first coupling means. Thus, a unit, which is simple to handle is provided which unit may be used with existing ostomy equipment.

The folding of the inner bag liner minimises the risk of "pancaking" and blocking of the bag as the inner bag liner is automatically gradually unfolded or stretched by the output from the stoma first contacting the bottom of the inner bag liner and pressing the same down into the receiving bag.

The inner bag liner is provided with folding lines for compacting the bag length-wise. The folding lines may suitably form spiral lines, which ensures that output from the stoma is disposed directly to the bottom of the inner bag liner causing an unfolding only exposing the sides thereof after filling the lower parts which reduces the risk of adherence to the sides of the inner bag liner.

In another embodiment of the invention the folding lines of the inner bag liner form bellows as well as spiral lines when compacting the bag lengthwise.

In yet another embodiment of the invention the folding lines of the inner bag liner form telescopic bellows as well as spiral lines when compacting the bag length-wise.

The folding lines form spiral lines as the bag is compacted in a lengthwise rotational movement. In one embodiment the folding lines are three-dimensional in the twisted state (i.e. the spiral lines), while they are two-dimensional (i.e. defined in one plane) in the unfolded state. As the inner bag liner is compacted by twisting a bottom part in relation to a rim of the bag it is possible to compact the bag in a way which avoids pancaking. In some embodiments the twisting is performed while a mandrel is inserted into the bag. When the bag unfolds the bag will 'de-twist'.

For keeping the disc-shaped member in a compact conformation, for easy handling and for protecting the inner bag liner before use it is suitable to provide the closed end of the compacted inner bag liner with a cover.

According to a THIRD ASPECT the present invention relates to a method for the preparation of an inner bag liner having folding lines which form spiral lines when the bag is compacted in a lengthwise rotational movement, said method comprising providing an inner bag liner, providing a mandrel placed movably on a base plate and being equipped with openings connected to a vacuum source, locating the inner bag liner sealingly against the base plate with the mandrel projecting into the inner bag liner, evacuating the air from the space between the inner bag liner and the mandrel, and retracting the mandrel in a lengthwise rotational movement such that the bag is compacted and the folding lines define spiral lines.

The mandrel may be movable with two degrees of freedom; a first degree allowing lengthwise movement in and out of a hole in the base plate and a second degree allowing rotation around the length axis of the mandrel. Thus, if a bottom part of the inner bag liner is retained at the tip of the mandrel and at the same time a rim part of the inner bag liner is retained at the base plate, it is possible to twist the bottom part of the inner bag liner in relation to the rim part of the inner bag liner when the mandrel is rotated around the length axis. If at the same time the mandrel is moved such that the tip is moved closer to the base plate, the bottom part of the bag is both rotated in relation to and moved closer to the rim part of the inner bag liner.

The bottom part of the inner bag liner may be retained at the tip of the mandrel by means of a mechanical engagement e.g. by pressing another object against the tip of the mandrel or by means of providing a vacuum at the tip. If vacuum is also provided along the sides of the mandrel it is advantageous to provide a bigger vacuum at the tip of the mandrel in order to retain the bottom part of the bag while the mandrel is rotated.

In a FOURTH ASPECT, the invention relates to a disposable inner bag liner for receiving effluents or waste products of the body and for use together with an ostomy appliance comprising an adhesive wafer to be attached to the wearer's abdomen, back, or chest, and a receiving member having a hole for receiving wastes exiting the stoma, ureter or catheter; said disposable inner bag liner having a hole for receiving wastes exiting the stoma, ureter or catheter and being capable of forming a bag inside the receiving member and being releasably attachable to the adhesive wafer in a first coupling area by first coupling means, the first coupling means being in the form of an adhesive flange projecting from a rim of the hole and having a surface for releasable sealing against a surface of the adhesive wafer, wherein the inner bag liner is provided with folding lines for compacting the bag lengthwise, and wherein said folding lines form spiral lines when the bag is compacted in a lengthwise rotational movement.

The disposable inner bag liner of the invention may be used together with existing ostomy devices one-piece ostomy appliances and also together with existing two-piece ostomy appliances, such as appliances comprising a base plate and a receiving member releasably attached via matching adhesive flanges or via matching coupling rings. A preferred such use is together with one-piece appliances or together with two-piece appliances wherein a base plate and a receiving member are attached via matching adhesive flanges. A disposable inner bag liner of the invention may be used together with appliances having very flexible such flanges without compromising the overall flexibility provided that the ring-shaped element and the flange show at approximately least the same flexibility as the adhesive flanges.

Thus, the inner bag liner is suitably made from a thin, water-impermeable sheet, which is not gas-tight. The bag liner is suitably in the form of a co-extruded or laminated sheet having a layer of water-soluble material such as PVA, PVAL or EVAL at the outer surface. The inner surface may suitably be made from a material, which may be processed into a thin layer without pinholes such as PE, EVA, PVC, PP, or a polyester which layer is impermeable for water vapour. The outer material may e.g. be in the form of a sheet or a non-woven material.

An inner bag liner of the invention may be made from a material being permeable for gas and thus permitting intestinal gasses entering the bag to diffuse through the inner bag liner without giving rise to ballooning for management by a conventional gas venting and filtering system placed on the outer bag. The inner bag liner is preferably impermeable to water and water vapour in order to avoid leaking of liquid or passing of water vapour which would start a deterioration of the outer layer of the bag liner.

The disposable inner bag liner of the invention may be provided so that the bottom part of the bag is rotated less than one revolution in relation to the rim part of the inner bag liner.

The disposable inner bag liner of the invention may be provided so that the bottom part of the bag is rotated less than three quarters of a revolution in relation to the rim part of the inner bag liner.

The disposable inner bag liner of the invention may be provided so that the bottom part of the bag is rotated less than two quarters of a revolution in relation to the rim part of the inner bag liner.

The disposable inner bag liner of the invention may be provided so that the bottom part of the bag is rotated less than one quarter of a revolution in relation to the rim part of the inner bag liner.

An inner bag liner may be produced by a manner known per se for producing bags such as blowing and welding or by cutting separate walls which are then sealed along the rim in a manner known per se, e.g. using an adhesive or by welding. When producing the inner bag liner it is suitably taken into account to provide a shape, which is readily folded afterwards in a manner known per se for providing bellows, telescopic bellows and/or spiral lines.

In a FIFTH ASPECT the invention relates to a method of applying an ostomy appliance to an ostomate, the ostomy appliance comprising: a base plate, said base plate having a first hole for receiving a stoma, ureter, or catheter and an adhesive wafer having a first surface to be attached to the wearer's abdomen, back, or chest; a receiving member or bag releasably attachable to the base plate, said receiving member having a second hole for receiving wastes exiting the stoma, ureter or catheter; and a disposable inner bag liner forming a second bag inside the receiving member and being releasably attachable to the base plate, said disposable inner bag liner having a third hole for receiving wastes exiting the stoma, ureter or catheter, said inner bag liner being compacted lengthwise to form a disc-like structure, and said inner bag liner being attachable releasably to the base plate in a first coupling area by first coupling means and the receiving member being attachable releasably to the base plate by second coupling means, the first coupling means being in the form of an adhesive flange projecting from the rim of the third hole and having a surface for adhesive sealing against a second surface of the base plate facing away from the user, wherein the inner bag liner is provided with folding lines for compacting the bag length-wise, and wherein said folding lines form spiral lines when the bag is compacted in a lengthwise rotational movement, said method comprising locating the stoma and applying the base plate, locating the inner bag liner, applying and sealing the same to the first coupling area, removing a release liner covering the first coupling means if present, and attaching the receiving member to the base plate.

In the following features and/or elements of the first, second, third, fourth and fifth aspect of the present invention is described in further detail.

An adhesive wafer for a body side member or of a 1-piece ostomy appliance bag according to the invention may comprise a medical grade barrier adhesive known in art the such as the formulation being disclosed e.g. in U.S. Pat. Nos. 4,367,732, 5,051.259, 5,714,225, 6,171,594, 6,303,700, 6,451,883, or 6,437,038, or in WO Application Nos. 00/54820, or 01/05340. For a 2-piece ostomy appliance according to the invention the body side member and the receiving member are provided with matching coupling means.

A coupling means may be any system known per se for attaching receiving bags to ostomy body side members and may suitably be matching coupling rings of the type disclosed in WO 93/18725, WO 94/18919, WO 91/01118, WO 91/01119 or matching flanges for adhesive connection of the type disclosed in U.S. Pat. No. 5,800,415, WO 00/30576, or WO 01/54632.

A carrier sheet present on the surface of the adhesive wafer facing the bag may be any suitable thermoplastic material known per se for use in the preparation of ostomy appliances e.g. a foam, a non-woven layer or a polyurethane, polyethylene, polyester or polyamide suitable for attachment of a receiving member using an adhesive or by welding.

A collection bag may be made in analogy with and from materials conventionally used for the preparation of ostomy appliances. Such materials are suitably films composed of any suitable material, which is heat sealable and sufficiently impervious for unpleasant odours such as polyolefin films or combinations of such films, e.g. polyethylene or a co-extrudate of polyethylene and polyvinylidene chloride. Suitably the bag is made from front and rear walls welded in a manner known per se along the rim forming a bag. When cutting or punching the walls, an opening for receiving a stoma is suitably also punched in the wall to form the rear wall.

A protective cover or release liner may for instance be siliconized paper. The protective cover is not present during the use of the ostomy appliance of the invention and is therefore not an essential part of the invention.

In a SIXTH ASPECT, the invention relates to a bag comprising a bottom part and a sidewall extending form the bottom part to a rim of the bag, the bag being compacted lengthwise while twisting the bottom part in relation to the rim such that folding lines defined by at least a part of the sidewall, define spiral lines when the bag is in the compacted state.

In one embodiment the spiral lines (which are defined by the folding lines when the bag is twisted) are three dimensional, whereas folding lines are two-dimensional when the bag is in the unfolded state.

The bag may be any bag such as an inner bag liner, a shopping bag, a garbage bag, etc. One advantage of the sixth aspect is that by compacting the bag by twisting, it is possible to provide a bag which will easily be able to unfold when material e.g. waste material enter the bag and thus apply pressure to the bottom part of the bag. Thus, it is possible to control the unfolding of the bag.

In one embodiment the folding lines extend from the bottom part to the rim. In a further embodiment the bottom part is substantially plane when the bag is in the compacted state.

The bag may be an inner bag liner.

In one embodiment the bag is suitable as an inner bag liner.

In another embodiment the bag is used as an ostomy bag.

A SEVENTH ASPECT of the present invention relates to a method for compacting a bag according to fifth or sixth aspect, said method comprising providing a bag, providing a mandrel placed movably on a base plate and being equipped with openings connected to a vacuum source, locating the bag sealingly against the base plate with the mandrel projecting into the bag, evacuating the air from the space between the bag and the mandrel, and retracting the mandrel in a lengthwise rotational movement such that the bag is compacted and folding lines in the sidewall of the bag define spiral lines.

The description of the sixth aspect also applies to the seventh aspect of the present invention.

The description of the third aspect also applies to the sixth and the seventh aspect of the present invention.

DETAILED DESCRIPTION OF THE INVENTION

An embodiment of the invention will now be described in details with reference to the drawing in which:

FIG. 3a shows the embodiment of FIG. 2 during the first step of detachment, FIG. 3b show attachment of the flanges of the invention.

BEST MODE OF CARRYING OUT THE INVENTION

The invention is now explained in more detail with reference to the drawings showing preferred embodiments of the invention.

Figure 1:
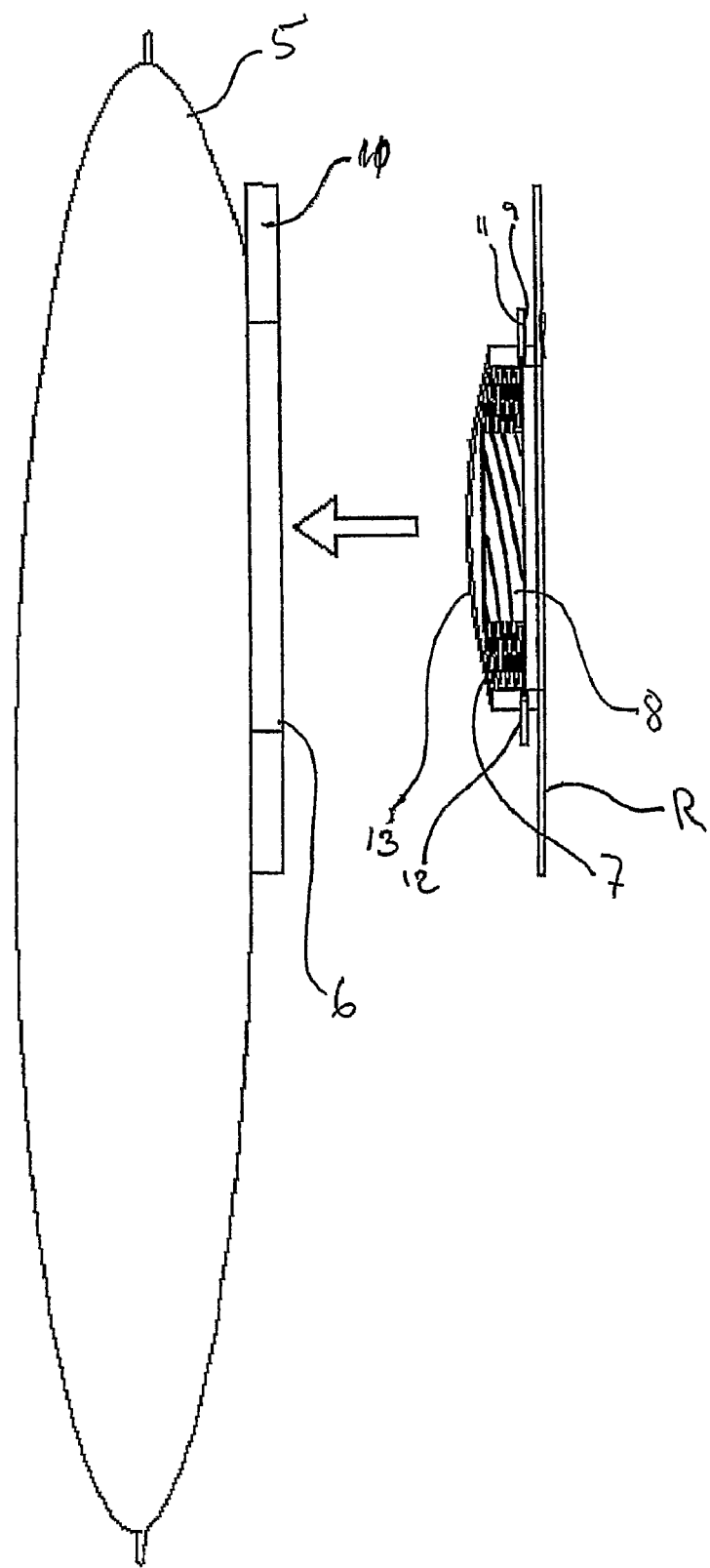
FIG. 1 shows parts of an embodiment of an ostomy appliance of the invention.
Figure 2:
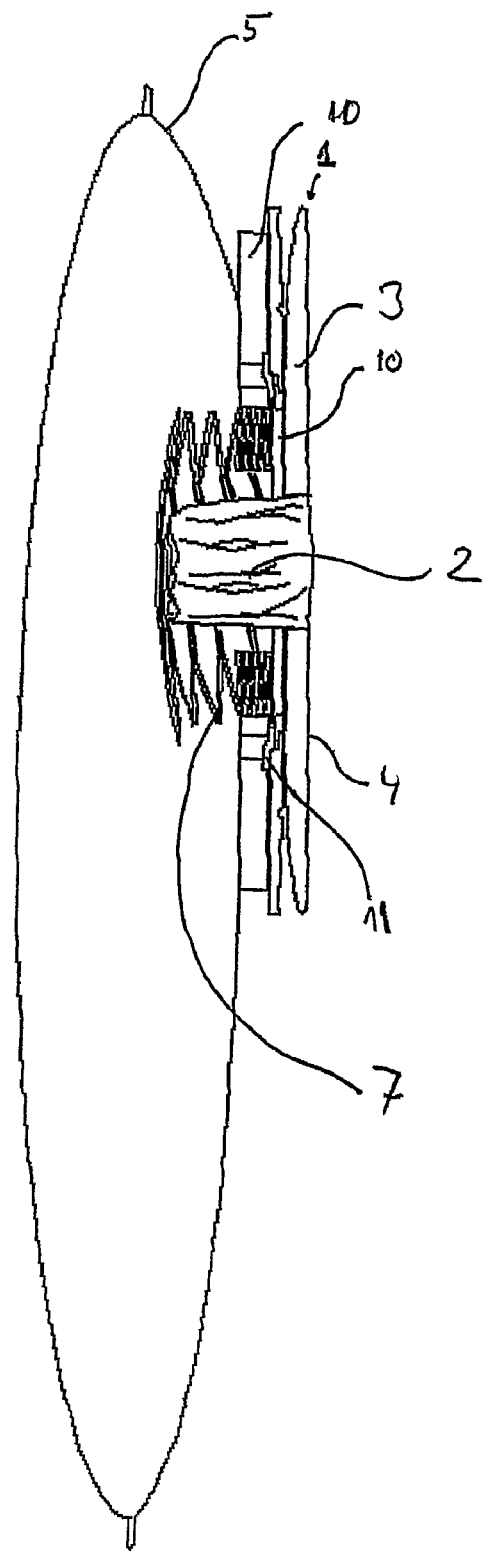
FIG. 2 shows the parts shown in FIG. 1 after assembly with a base plate and applied to the user's skin

Reference is made to FIGS. 1 and 2 showing an ostomy appliance comprising an base plate, said base plate 1 having a first hole for receiving a stoma 2, ureter, or catheter and an adhesive wafer 3 having a first surface 4 attached to the wearer's abdomen (not shown), back, or chest; a receiving member or bag 5 releasably attached to the base plate, said bag having a second hole 6 for receiving wastes exiting the stoma, ureter or catheter; and a disposable inner bag liner 7 forming a second bag inside the receiving member and being releasably attached to the base plate, said disposable inner bag liner having a third hole 8 for receiving wastes exiting the stoma, ureter or catheter and being attached releasably to the base plate in a first coupling area 9 by first coupling means and the receiving member being attached releasably to the base plate by second coupling means in the form of an adhesive flange 10 wherein the first coupling means is in the form of an adhesive flange 11 projecting from the rim of the third hole and having a surface for adhesive sealing against a second surface of the base plate facing away from the user and the flange 10.

In FIG. 1 the inner bag liner is shown in the form of a disc-shaped member in which the inner bag liner is compacted lengthwise and covered by a cover 13 secured to the flange 11 and a release liner R covering the adhesive surface 9.

In FIG. 2 the inner bag liner and the receiving member are assembled and applied to a base plate placed on the user's skin (not shown) with the stoma projecting into the inner bag liner and the receiving member. As appears, the top of the stoma presses the inner bag liner into the receiving member. The flange 10 of the receiving member is adhesively secured and sealed to a flange 18 on the base plate.

In FIG. 3a is shown the embodiment shown in FIG. 2 at the end of the service period during detachment of the receiving member and with the inner bag liner in a stretched state with the its contents 14 received from the stoma. The cover 13 is detached and situated in the bottom of the receiving member 5, which is detached from the base plate. The inner bag liner is still attached to the base plate and is in the course of being pulled out from the receiving member.

In FIG. 3b is shown a flange 18 of the base plate, a flange 10 of the receiving member (second coupling means) and a flange 11 of the inner bag liner (first coupling means). The flange 11 is releasably attached to the flange 18 of the base plate in a first coupling area 24. The flange 10 of the receiving member is releasably attached to the flange 18 of the base plate in a second coupling area 22 and to the flange 11 of the inner bag liner in a third coupling area 20. When removing the flange 10 of the receiving member the adhesive forces between the flange 11 of the inner bag liner and the flange 18 of the base plate are stronger than the adhesive forces between the flange 10 of the receiving member and the flange 11 of the inner bag liner. Thus, the flange 11 of the inner bag liner is not removed at the same time. Accordingly it is possible to remove the receiving member and leave the inner bag liner be attached whereby it serves as a drip catcher. The adhesive forces between the flange 10 of the receiving member and the flange 11 of the inner bag liner is reduced so as to be smaller than the adhesive forces between the flange 11 of the inner bag liner and the flange 18 of the base plate by providing the flange 11 with a siliconized surface on the side facing the flange 10 in the third coupling area 20.

Figure 4:
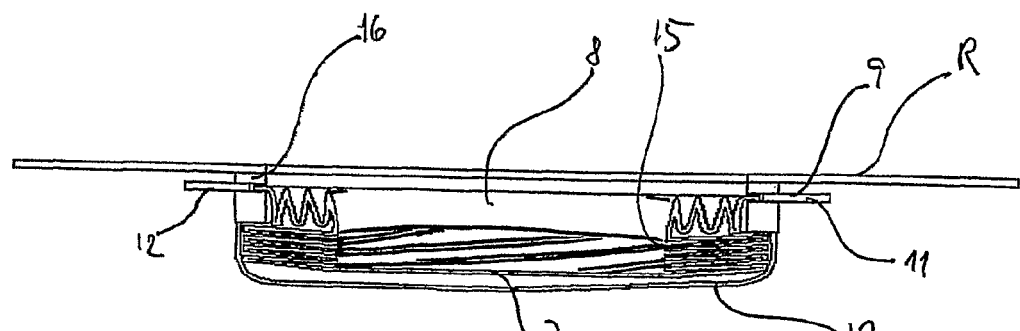
FIG. 4 shows an embodiment of a disposable inner bag liner of the invention.
Figure 5:
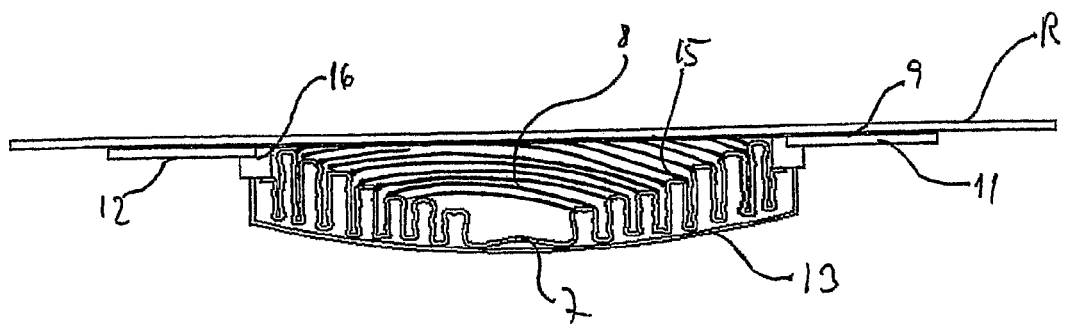
FIG. 5 shows another embodiment of a disposable inner bag liner of the invention.
Figure 6:
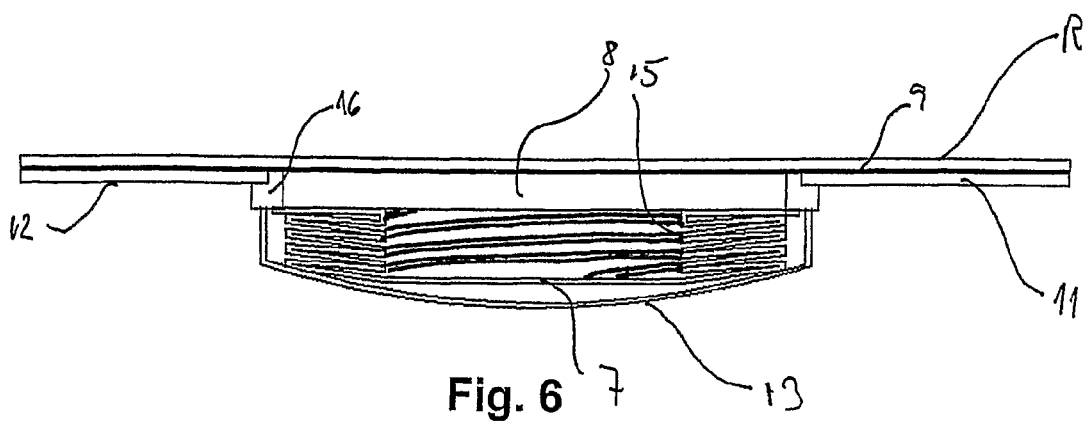
FIG. 6 shows a third embodiment of a disposable inner bag liner of the invention.

In FIGS. 4-6 are shown alternative embodiments of a disposable inner bag liner of the invention in the form of various compacted disposable disc-shaped members for receiving effluents or waste products of the body.

The compacted disposable inner bag liner members comprise an inner bag liner 7 having a hole 8 for receiving wastes exiting the stoma, ureter or catheter and a first coupling area by first coupling means wherein the first coupling means is in the form of an adhesive flange 11 projecting from the rim of the hole 8 and having a surface 9 for adhesive sealing against a surface of a base plate, said adhesive surface being covered by a release liner R. The flange 11 has an adhesive surface 12 for releasable sealing against a flange of a receiving member and is covered by a cover 13. The inner bag liner 7 and the flange 11 are secured to a ring-shaped element 16 stabilising the rim of the hole 8. A further ring-shaped element 17 located between the cover 13 and the flange 11 is shown in FIG. 4.

The inner bag liner comprises a folded part 15 folded in different manners. In FIGS. 4 and 6 is shown an inner bag liner folded forming spiral lines for lengthwise expansion, and in FIG. 5 is shown an inner bag liner folded forming a telescopic bellows in combination with spiral lines. Furthermore, different embodiments of the ring-shaped element 16 are shown in FIGS. 4-6. The ring-shaped element may be made from a single or more materials as found suitable for the purpose, typically a foam material showing the desired flexibility and is suitably made from a biodegradable foam material.

Still further, different embodiments of the flange 11 are shown. The flange shown in FIG. 4 is relatively narrow and is suitable for use together with two-piece appliances, especially two-piece appliances comprising matching coupling rings for attachment of a receiving member to the base plate, for which purpose, it is suitable that the flange is not interfering with the coupling area of the coupling rings. The embodiments shown in FIGS. 5 and 6 have broader flanges and are suitable for use together with two-piece appliances comprising matching adhesive flanges for attachment of a receiving member to the base plate or together with one-piece appliances.

Thus, the disc-shaped member of the invention may in one embodiment comprise the elements a)-f) starting from the side of the cover:

a) A relatively large transparent release liner (R) rendering it possible to see through the release liner during assembling the disc-shaped member and a receiving member to ascertain whether the disc-shaped member is located correctly (centrally) before the disc-shaped member is brought into sealing contact with flange of the receiving member.

The release liner may advantageously have an external diameter corresponding to the external diameter of the flange of the receiving member.

b) A flexible and biodegradable or water-soluble adhesive located on the surface of the ring-shaped member (16) and or the flange (11) facing a base plate for securing the inner bag liner to the base plate during removal of the receiving member, c) A flange (11) made from a biodegradable or water-soluble material such as a foam material. This flange suitably shows releasing properties at the surface (12) enabling a releasable sealing against the adhesive of the flange (10) of the receiving member. Thus, the disc-shaped member may be repositioned on the flange (10) if necessary, and is secured to the flange of the receiving member so that the user does not risk losing the disc-shaped member during application of the receiving member to the base plate, d) A folded, biodegradable or water-soluble inner bag liner (7), e) A further ring-shaped element (17) which together with the hole (6) of the receiving member ensures a centering of the disc-shaped member, and f) A biodegradable or water-soluble protecting cover (13).

In this embodiment, the risk of damaging the adhesive at the flange of the receiving member is reduced to a very high degree as the surface (12) of the flange (11) shows release-properties rather than adhesive properties.

In an alternative embodiment the disc-shaped member of the invention may comprise the following elements starting from the side of the release liner:

1) A relatively large transparent release liner (R) as stated above,

2) A biodegradable or water-soluble flange (11), e.g. a flange of foam, having a larger diameter and so as to allow adhesive engagement in the first coupling area (9) of the surface with at least a part the adhesive flange (18). This flange suitably shows releasing properties at the surface (12) as stated above, 3) A folded, biodegradable or water-soluble inner bag liner (7), and 4) A biodegradable or water-soluble protecting cover (13).

When using an appliance according to the invention, typically the following steps are carried out:

Step 1: Applying and sealing the disc-shaped member to the flange of the receiving member. The diameter of the release liner suitably corresponds to the diameter of the coupling flange of the receiving member for facilitating the location using the rims of the flange and of the release liner for centering the disc-shaped member.

Alternatively, the flange of the disc-shaped member is transparent and has a diameter greater than the hole of the receiving member, and in this case the transparency of the release liner is utilised for ascertaining that the flange has sufficient contact to the coupling flange of the receiving member.

Step 2: After securing the disc-shaped member to the receiving member, the release liner is removed and the cover is suitably detached from the flange of the disc-shaped member by pressure from e.g. a finger for unfolding the inner bag liner sufficiently to accommodate the stoma in question, and the receiving member is attached to the base plate in the conventional manner according to the type of coupling means.

Step 3: The inner bag liner is automatically unfolded gradually according to the output from the stoma. The first output from the stoma will contact the inner bag liner at the bottom, which again will reduce the risk of "pancaking".

The inner bag liners of the state of the art are applied in an unfolded state and this will increase the risk of "pancaking", especially when used for colostomies as the output comprises very little water and will adhere to the top of the bag and not fall into the bag.

Step 4: During substitution the receiving member is detached in the usual manner and the inner bag liner is designed so as to ensure that it is easily withdrawn from inside the receiving member through the centre hole of the coupling flange.

Step 5: The adhesive at the flange of the disc-shaped member ensures that the inner bag liner stays adhered to the base plate. The inner bag liner acts as a drip-catcher and a fresh inner bag liner may be attached to the receiving member as in step 1 at leisure without risking escaping odour or soiling of the clothing by dripping output from the stoma.

Step 6: When the fresh inner bag liner and the receiving member are assembled, the used inner bag liner is detached and may be flushed in the WC using a single flush.

The base plate and the stoma may be cleaned in the usual manner and the receiving member provided with a fresh inner bag liner is applied.

Figure 8:
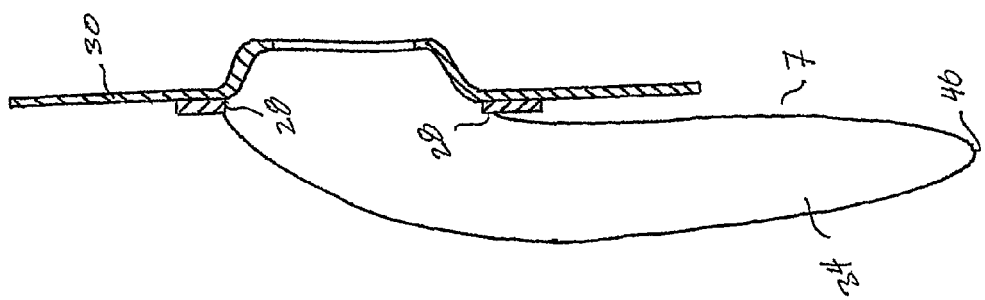
Figure 7:
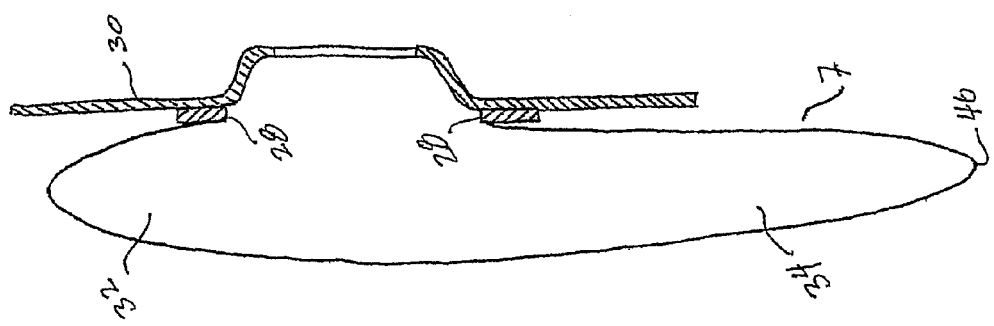

FIGS. 7 and 8 show two different embodiments of the disposable inner bag liner 7, in both figures the inner bag liner 7 is unfolded and releasably attached via the flange 28 to a disc 30 which in the use situation is removed such that the inner bag liner 7 may be releasably attached to a base plate (not shown). The disc 30 protects the inner bag liner when it is in the folded or twisted stage and serves as a release liner to which the flange 28 is adhered.

The disposable inner bag liner 7 in FIG. 7 is shaped such that it comprises an upper part 32 which (when the inner bag liner is unfolded) extends upwards in relation to the flange 28 and a lower part 34 which extends downwards in relation to the flange 28, when the inner bag liner is unfolded.

When inserting a mandrel 36 into the inner bag liner 7 it will extend into the lower part 34, and thus the upper part 32 in FIG. 7 will require special handling when the inner bag liner 7 is to be compacted or twisted. The mandrel 36 is provided with a plurality of vacuum holes 38 which in the use situation are in connection with a vacuum source (not shown). On the surface 40 of the mandrel 36 is provided a plurality of vacuum distributing cavities 42 which are used to make sure that the vacuum is distributed to areas of the surface 40 which are not close to the vacuum holes 38. Thereby it is avoided that a vacuum hole is blocked by the inner bag liner whereby the vacuum cannot be distributed to other parts of the surface 40.

Figure 9:
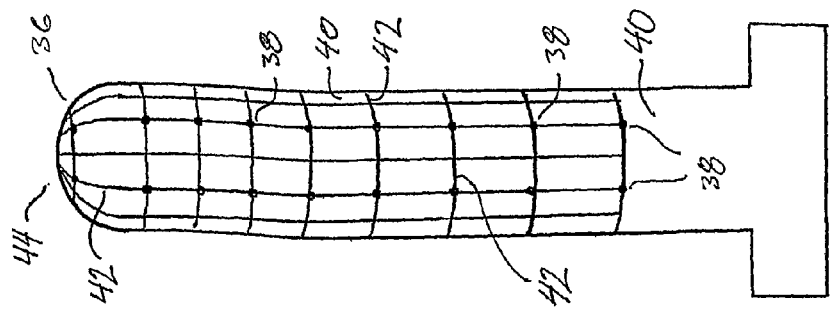
FIGS. 7-18 show different embodiments of compacting and/or twisting of the inner bag liner.

The surface of the mandrel 36 is as smooth as possible so as to ensure that the mandrel 36 does not by accident tear a hole in the inner bag liner 7. In the embodiment of FIG. 9 the tip 44 of the mandrel 36 is round but in some embodiments the tip is substantially flat so as to allow another object to be pressed against the substantially flat surface whereby it is possible to retain the bottom part 46 of the inner bag liner 7. In order to avoid tearing of the inner bag liner the transition zone between the substantially flat tip and the side surface may be rounded.

Figure 11A:
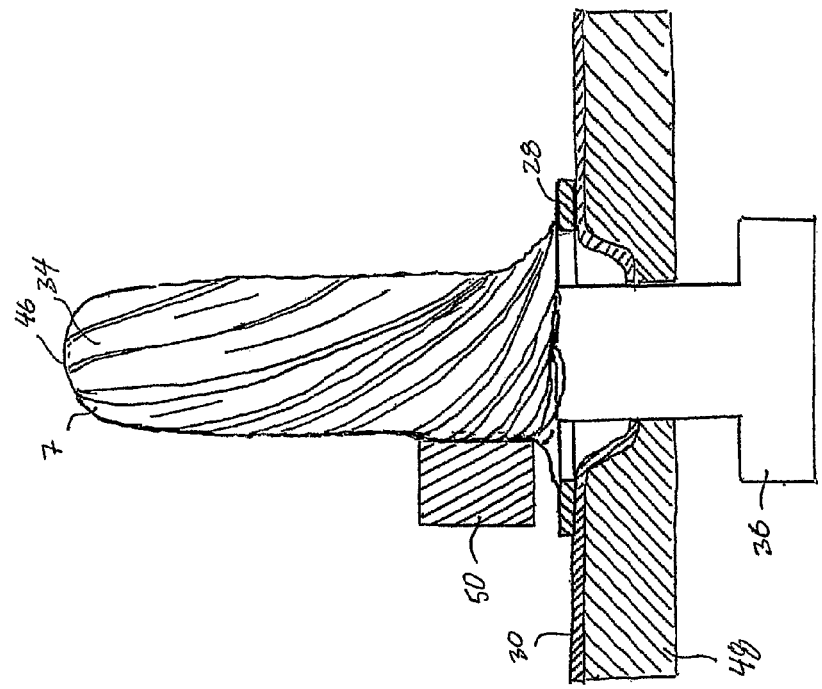
Figure 10:
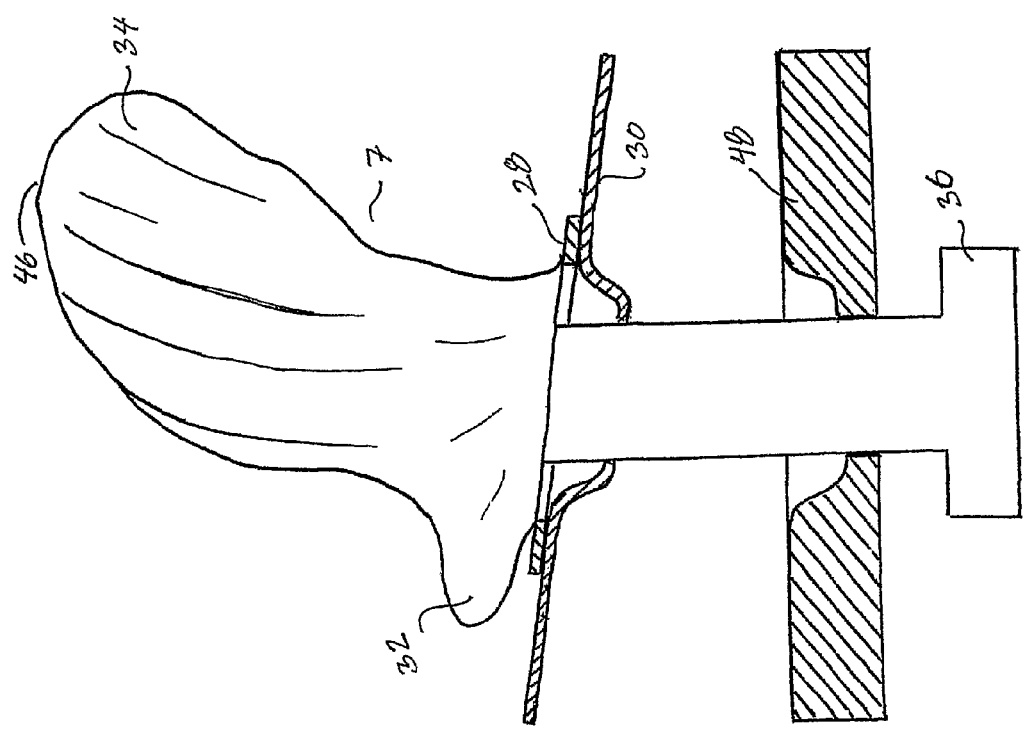

In FIG. 10 the mandrel 36 is inserted into the upper part 34 of the inner bag liner 7. As described above the upper part 32 requires special handling when compacting or twisting the inner bag liner 7. The disc 30 is retained in the tool 48 e.g. mechanically or by means of vacuum. The inner bag liner is twisted either by twisting/rotating the mandrel 36 and/or by twisting/rotating the tool 48. In order to make sure that the upper part 32 is also rotated around the mandrel 36 an interception means 50 is provided, as shown in FIG. 11a. The interception means 50 could be a brush, a scraper or a mob or an air stream or any other similar element or means. Thus, when the inner bag liner 7 is twisted, the interception means 50 pushes the upper part 32 towards the mandrel.

Figure 11B:
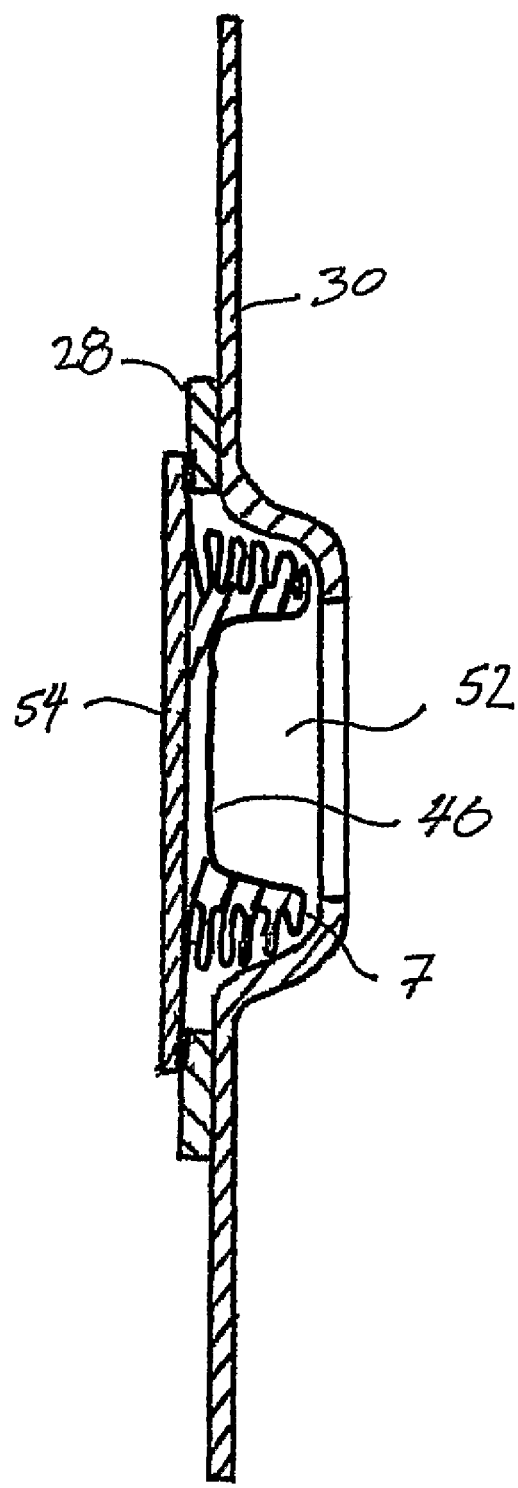

After the inner bag liner 7 has been twisted the mandrel 36 is pulled out of the inner bag liner whereby the inner bag liner is pulled down into the compartment 52 of the disc 30, as shown in FIG. 11b. Means for guiding the twisted inner bag liner into the compartment may be provided (not shown). A cover 54 is provided so as to retain the twisted inner bag liner in the compartment 52. In order to make sure that the bottom part 46 of the inner bag liner 7 is positioned as close as possible to the cover 54 (whereby it is easier for the inner bag liner to unfold in the use situation) the mandrel 36 is in a first stage not pulled completely out of the inner bag liner but rather to a position wherein the tip of the mandrel is aligned the flange 28. At the same time the means for guiding the twisted inner bag liner pushes the twisted part of the inner bag liner into the compartment 52. Another purpose of the cover 54 is to ensure that the adhesive of the outer receiving member does not adhere to the inner bag liner when the inner bag liner is being attached to the outer receiving member.

Figure 12:
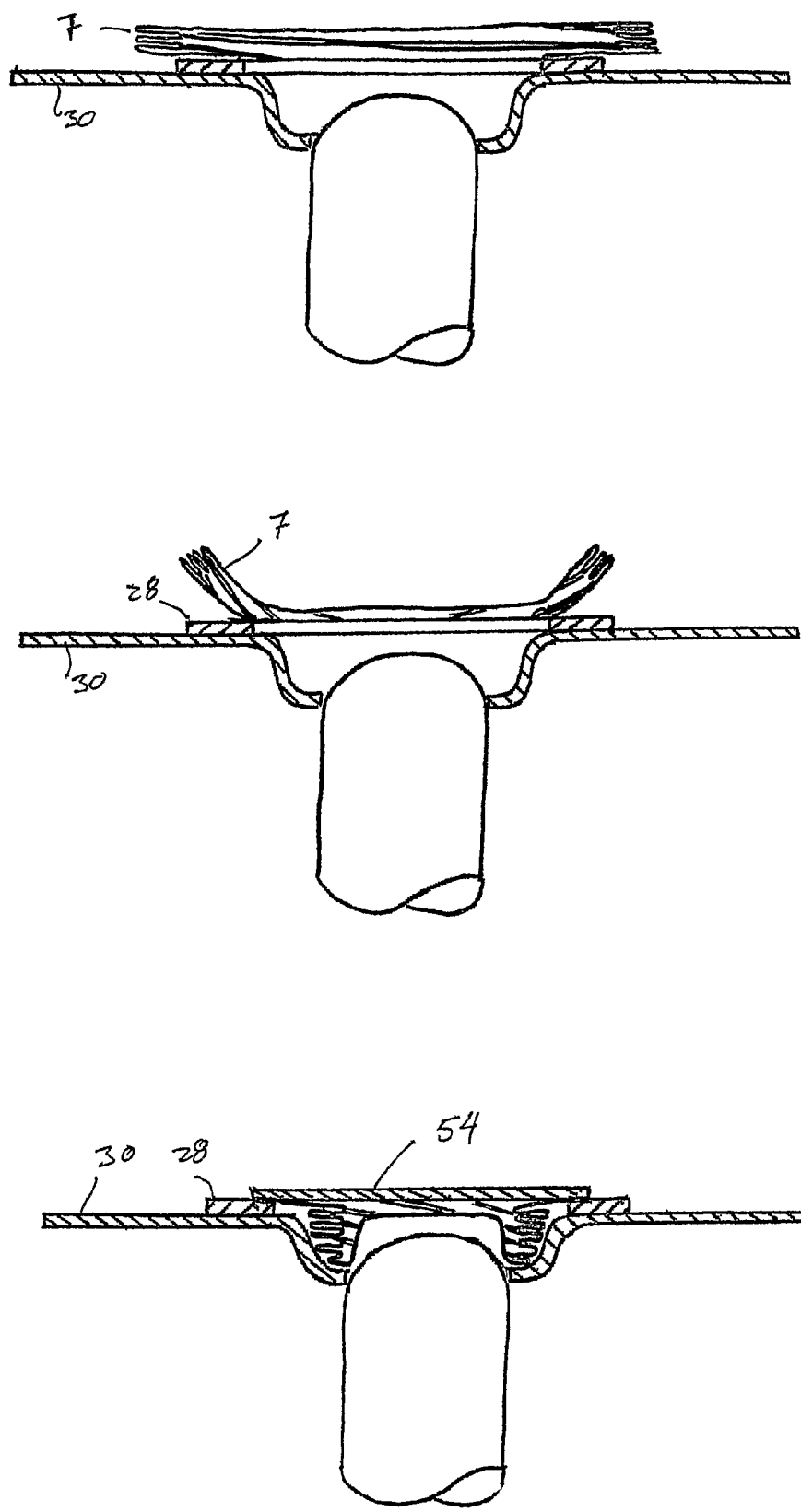

FIG. 12 shows the steps of folding the compacted inner bag liner into a compartment and provide it with a cover 54.

Figure 13:
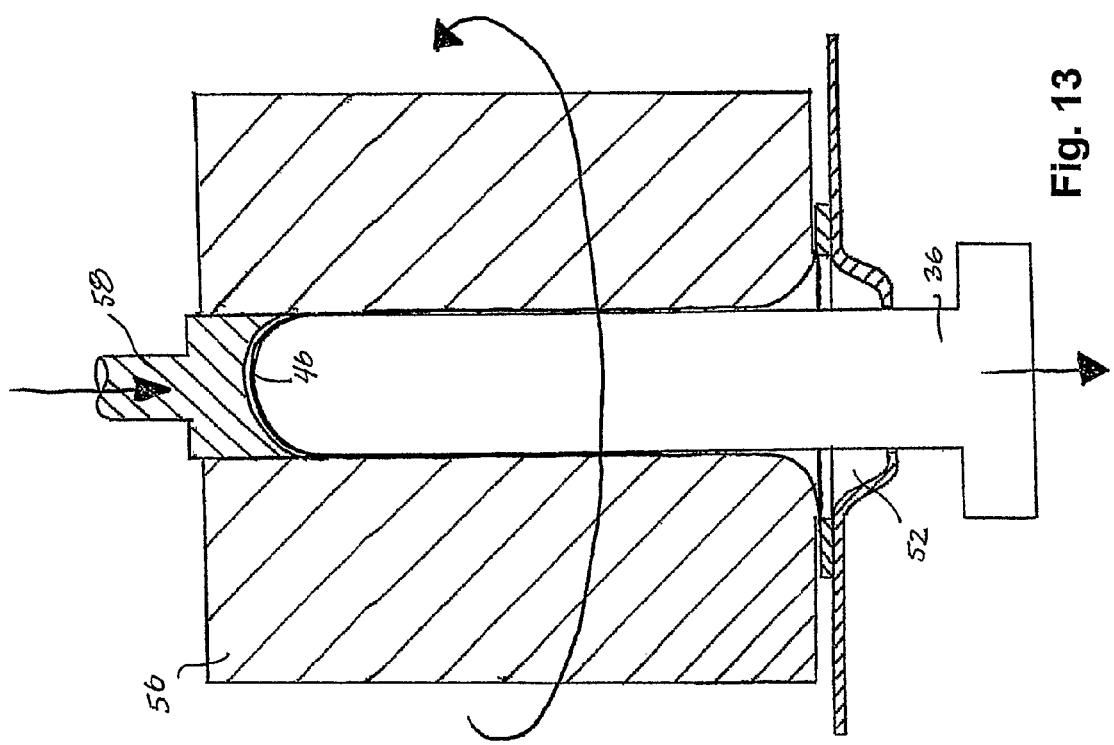
Figure 16:
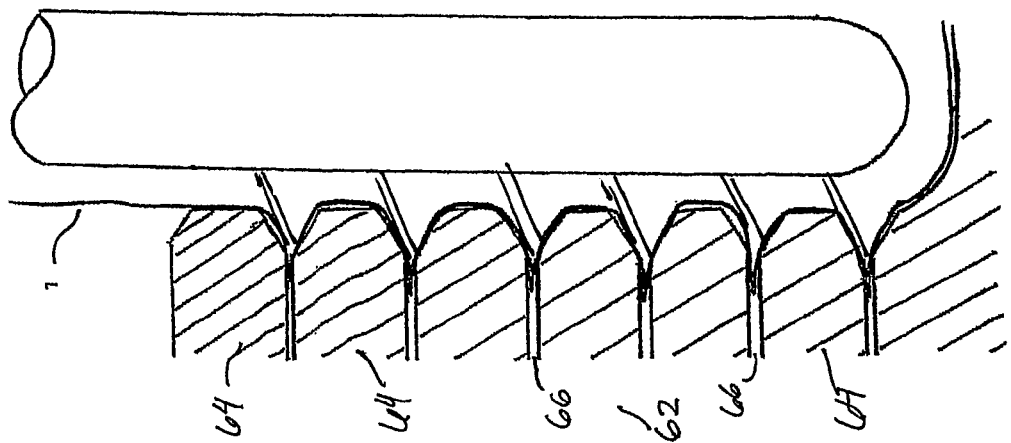

In the embodiment of FIG. 13 the inner bag liner 7 is twisted by means of an outer rotation tool 56 which is rotated prior to pulling the mandrel 36 out of the inner bag liner 7. In some cases the tool 56 is also rotated while pulling out the mandrel and in yet other cases the tool 56 is not rotated at all but merely serves as a means making sure that the inner bag liner follows the mandrel closely. Furthermore, a tip retaining element 58 may be provided, which is used to retain the bottom part 46 of the inner bag liner in relation the mandrel. The tip retaining means may also rotate while twisting the bag and/or removing the mandrel. The mandrel may also rotate while twisting the bag e.g. could rotate while the tool 56 is not rotating.

Figure 14:
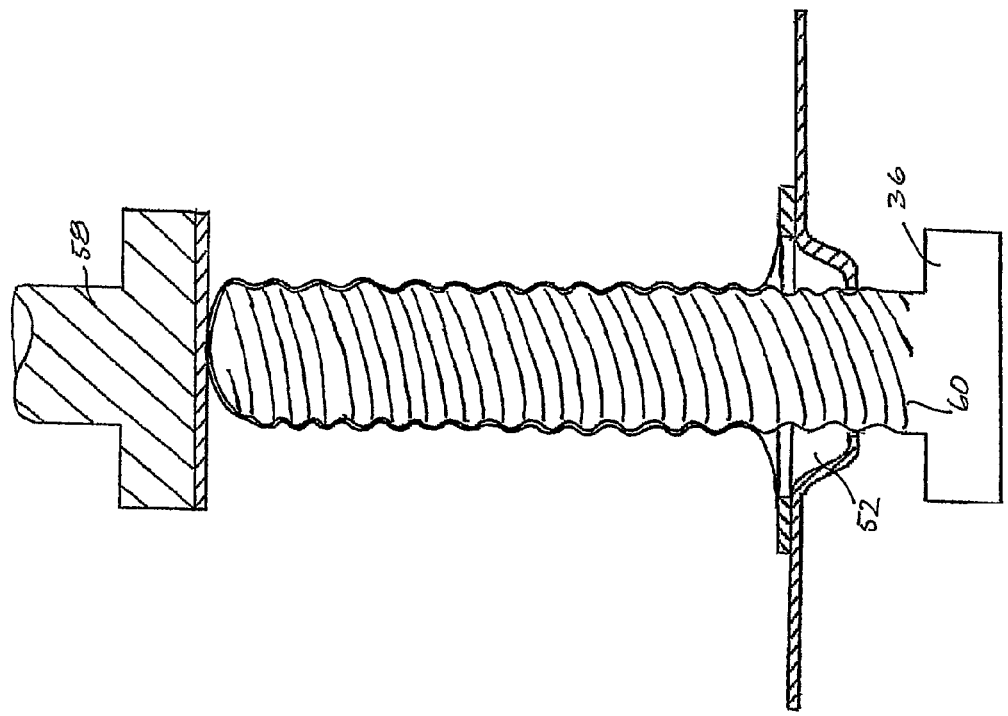

In a further embodiment shown in FIG. 14 the mandrel 36 has a screw thread pattern 60 on the surface such that when the mandrel 36 is pulled out of the inner bag liner 7 it is rotated and the inner bag liner is moved into the compartment 52. A tip retaining element 58 may be provided and be used to retain the tip either mechanically or by means of vacuum.

Figure 15:
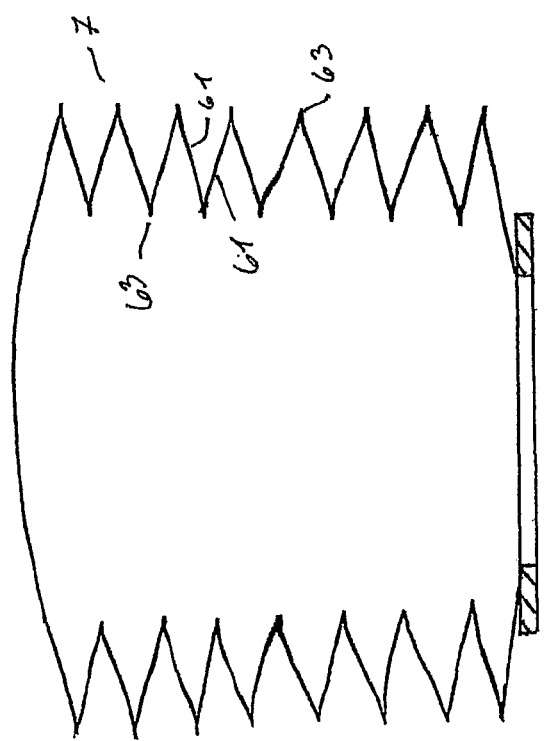

In some embodiments the inner bag liner in the unfolded state is provided as bellows as shown in FIG. 15. Such bellows may be provided by attaching a plurality of rings 61 together or by means of a bellows providing tool 62. The rings may be attached to each other in points of attachment 63. The points of attachment 63 may be provided by means of glue, laser welding, heat welding or ultrasonic welding.

The bellows providing tool 62 may comprise a plurality of co-operating fold providing rings 64 which when pressed together provides a fold in the inner bag liner. The fold providing rings 64 may be heated. In order to force the inner bag liner into the gap 66 between the fold providing rings 64 the inner bag liner may be inflated by providing a pressure inside the inner bag liner 7. The bellows are combined with spiral lines.

Figure 17:
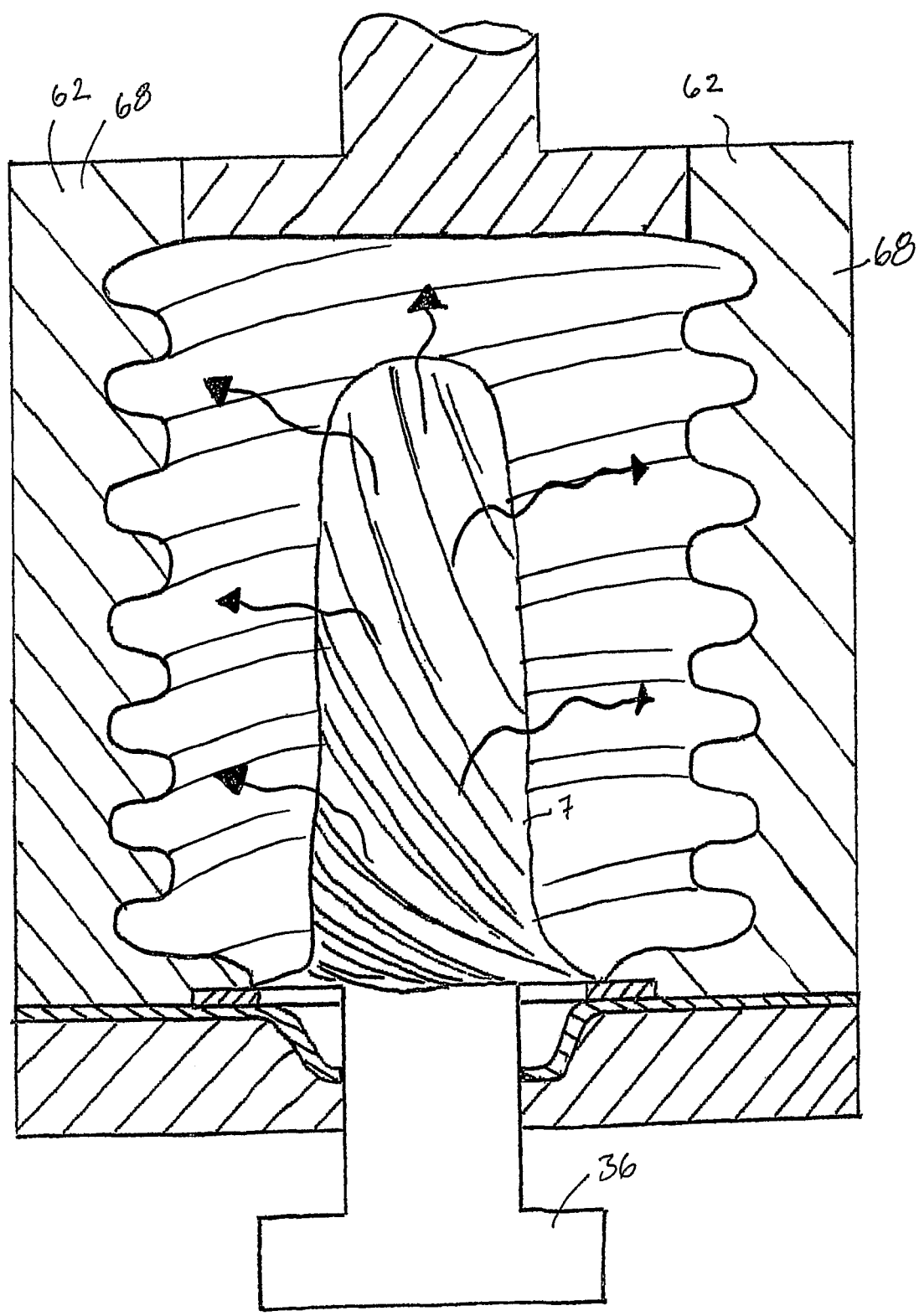
Figure 18:
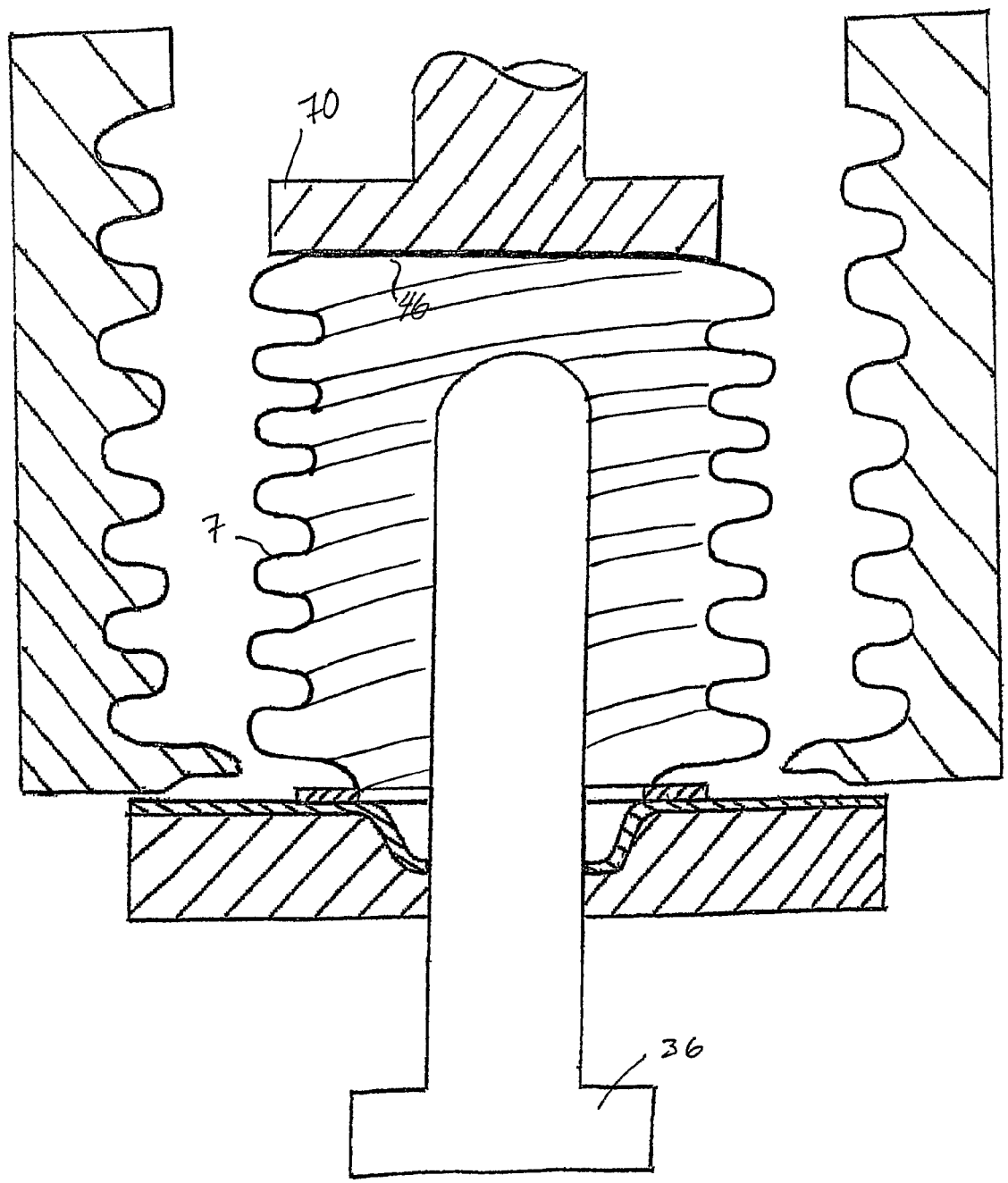

In another embodiment the bellows providing tool 62 is provided as a two or more parts 68 which when moved together define a bellows like shape as shown in FIG. 17. The bellows providing tool is provided with spiral lines. In this case the inner bag liner 7 is inflated and the heated parts define the bellows in the inner bag liner. Afterwards parts 68 are moved away from each other as shown in FIG. 18 and a piston 70 presses the inner bag liner in to a shape shown in the upper part of FIG. 12. The next step is to fold compacted inner bag liner as shown in FIG. 12 and provide a cover 54. The piston 70 may be provided with vacuum providing means such that the bottom part 46 can be retained.

The invention claimed is:

1. An ostomy appliance comprising:
    a base plate, said base plate having a first hole for receiving a stoma, ureter, or catheter and an adhesive wafer having a first surface to be attached to the wearer's abdomen, back, or chest;
    a receiving member releasably attached to the base plate, said member having a second hole for receiving wastes exiting the stoma, ureter or catheter; and
    a disposable inner bag liner forming a second bag inside the receiving member and being releasably attachable to the base plate in a first coupling area by a first coupling element, said disposable inner bag liner having a third hole for receiving wastes exiting the stoma, ureter or catheter and the receiving member being releasably attachable to the base plate in a second coupling area by a second coupling element, the first coupling element being in the form of an adhesive flange projecting from a rim of the third hole and having a surface for releasable sealing against a second surface of the base plate facing away from the user,
    said inner bag liner being provided with spiral-shaped folding lines for compacting the bag lengthwise while also subjecting the bag to rotational twisting movement when the bag is compacted, said spiral-shaped folding lines avoiding pancaking of the bag and causing the bag to untwist as it is unfolded during use.

2. The ostomy appliance according to claim 1, wherein the second coupling element is in the form of an adhesive flange projecting from the rim of the second hole and having a surface for adhesive sealing against the second surface of the base plate.

3. The ostomy appliance according to claim 2, wherein the outer diameter of the first coupling element is greater than the inner diameter of the second coupling element.

4. The ostomy appliance according to claim 2, wherein the peel strength of the adhesive sealing of the first coupling element is greater than the peel strength of the second coupling element.

5. The ostomy appliance according to claim 3, wherein the second coupling element of the receiving member in a third coupling area is releasable attachable to the flange of the disposable inner bag liner and wherein the peel strength of the adhesive sealing in the first coupling area is greater than the peel strength in the third coupling area.

6. The ostomy appliance according to claim 4, wherein the flange of the inner bag liner is provided with a siliconized surface on the side facing the flange of the receiving member in the third coupling area.

7. The ostomy appliance according to claim 1, wherein the second coupling element is in the form of one or more coupling rings, and wherein the outer diameter of the first coupling element is smaller than the inner diameter of the second coupling element.

8. An ostomy appliance comprising:
an adhesive wafer, having a first hole for receiving a stoma, ureter, or catheter, said adhesive wafer having a first surface to be attached to the wearer's abdomen, back, or chest;
a receiving member attached to the adhesive wafer, said member having a second hole for receiving wastes exiting the stoma, ureter or catheter; and
a disposable inner bag liner inside the receiving member and being releasably attachable to the adhesive wafer by a first coupling element, said disposable inner bag liner having an open end with a third hole for receiving wastes exiting the stoma, ureter or catheter and a closed end opposite said open end forming a bottom part of said liner when the liner is unfolded, the first coupling element being in the form of an adhesive flange projecting from a rim of the third hole and having a surface for releasable sealing against a first surface of the adhesive wafer,
said inner bag liner being compacted in a lengthwise direction while said closed end is rotated relative to said open end to twist the bag liner such that spiral shaped folding lines are defined, said spiral-shaped folding lines avoiding pancaking of the bag and causing the bag to untwist as it is unfolded during use.

9. The ostomy appliance according to claim 8, wherein the inner bag liner is compacted lengthwise to form a disc-like structure having an outer diameter less than the inner diameter of the first coupling element.

10. The ostomy appliance as claimed in claim 8, wherein the folding lines of the inner bag liner form bellows as well as spiral lines when compacting the bag lengthwise.

11. The ostomy appliance as claimed in claim 8, wherein the folding lines of the inner bag liner form telescopic bellows as well as spiral lines when compacting the bag lengthwise.

12. The ostomy appliance according to claim 8, wherein the closed end of the compacted inner bag liner is provided with a cover.

13. A disposable inner bag liner for receiving effluents or waste products of the body and for use together with an ostomy appliance comprising:
an adhesive wafer to be attached to the wearer's abdomen, back, or chest, and
a receiving member having a hole for receiving wastes exiting the stoma, ureter or catheter,
said disposable inner bag liner having a hole for receiving wastes exiting the stoma, ureter or catheter and being capable of forming a bag inside the receiving member and being releasably attachable to the adhesive wafer in a first coupling area by a first coupling element, the first coupling element being in the form of an adhesive flange projecting from a rim of the hole and having a surface for releasable sealing against a surface of the adhesive wafer, said inner bag liner being provided with spiral-shaped folding lines for rotationally twisting a bottom of said bag relative to the rim thereof while compacting the bag lengthwise, said spiral-shaped folding lines avoiding pancaking of the bag and causing the bag to untwist as it is unfolded during use.

14. The disposable inner bag liner according to claim 8, wherein the inner bag liner is provided with a membrane allowing intestinal gas to escape from the inner bag liner but is impermeable to liquids.

15. The disposable inner bag liner according to claim 8, wherein said bottom part of the bag is rotated less than three quarters of a revolution in relation to the rim of the inner bag liner.

16. The disposable inner bag liner according to claim 8, wherein the bottom part of the bag is rotated less than two quarters of a revolution in relation to the rim of the inner bag liner.

17. The disposable inner bag liner according to claim 8, wherein the bottom part of the bag is rotated less than one quarter of a revolution in relation to the rim of the inner bag liner.

18. The ostomy appliance according to claim 8, further comprising a base plate which defines the first hole and includes the adhesive wafer.

19. The ostomy appliance according to claim 18, wherein the receiving member is releasably attached to the base plate.

20. The ostomy appliance according to claim 18, wherein the disposable inner bag liner is releasably attachable to the base plate in a first coupling area by the first coupling element.

21. The ostomy appliance according to claim 18, wherein the receiving member is releasably attachable to the base plate in a second coupling area by a second coupling element.

22. The ostomy appliance according to claim 18, wherein the base plate defines a second surface which, when the base plate is attached to the wearer's abdomen, back or chest, faces away from the user and wherein the adhesive flange of the first coupling element has a surface for releasable sealing against the second surface of the base plate.

23. The ostomy appliance according to claim 1, wherein said spiral-shaped folding lines are three-dimensional when the inner bag liner is compacted in twisted state and two-dimensional when the inner bag liner is unfolded in use.

24. The ostomy appliance according to claim 8, wherein said spiral-shaped folding lines are three-dimensional when the inner bag liner is compacted in twisted state and two-dimensional when the inner bag liner is unfolded in use.

25. The disposable inner bag liner according to claim 13, wherein said spiral-shaped folding lines are three-dimensional when the inner bag liner is compacted in twisted state and two-dimensional when the inner bag liner is unfolded in use.

* * * * *